(12) United States Patent
Paulos et al.

(10) Patent No.: US 8,852,133 B2
(45) Date of Patent: Oct. 7, 2014

(54) HYPEREXTENSION BRACE ASSEMBLY AND METHODS OF USE

(75) Inventors: Lonnie E. Paulos, Pensacola, FL (US); Kim A. Nelson, Salt Lake City, UT (US)

(73) Assignee: The Lonnie and Shannon Pavlos Trust, Salt Lake City, UT (US)

( * ) Notice: Subject to any disclaimer, the term of this patent is extended or adjusted under 35 U.S.C. 154(b) by 783 days.

(21) Appl. No.: 12/993,258

(22) PCT Filed: Jun. 3, 2009

(86) PCT No.: PCT/US2009/046183
§ 371 (c)(1),
(2), (4) Date: Nov. 18, 2010

(87) PCT Pub. No.: WO2009/149217
PCT Pub. Date: Dec. 10, 2009

(65) Prior Publication Data
US 2011/0071451 A1    Mar. 24, 2011

Related U.S. Application Data

(60) Provisional application No. 61/148,973, filed on Feb. 1, 2009, provisional application No. 61/058,555, filed on Jun. 3, 2008.

(51) Int. Cl.
*A61F 5/00* (2006.01)
*A61F 13/00* (2006.01)
*A61F 5/01* (2006.01)

(52) U.S. Cl.
CPC ............. *A61F 5/0123* (2013.01); *A61F 5/0106* (2013.01)
USPC ......... 602/26; 602/5; 602/23; 602/60; 602/62

(58) Field of Classification Search
CPC ... A61F 5/0585; A61F 5/0118; A61F 5/0111; A61F 5/0123; A61F 13/00; A61F 13/14; A61F 13/016; A61F 13/107; A61F 5/0113; A61F 5/0193; A61F 13/061; A61F 13/08
USPC .................. 602/16, 23, 5, 60–64, 20, 26–29; D24/190–192; 2/24
See application file for complete search history.

(56) References Cited

U.S. PATENT DOCUMENTS 2,603,786 A * 7/1952 Haines ................................ 2/24
4,240,414 A * 12/1980 Theisler ........................ 602/26
(Continued)

FOREIGN PATENT DOCUMENTS

EP       1462072      9/2004
JP       01150916     10/1989
(Continued)

OTHER PUBLICATIONS

WIPO International Searching Authority, International Search Report and the Written Opinion of the International Searching Authority of co-pending PCT Application No. PCT/US09/67152 to Lonnie E. Paulos.
(Continued)

*Primary Examiner* — Kim M Lewis
(74) *Attorney, Agent, or Firm* — John Brooks Law LLC; John J Brooks III

(57) ABSTRACT

Embodiments of the hyperextension brace assembly utilize a cross-strap attached to mounting facilities about a joint to limit the extension of limbs about the joint. The cross-strap assembly is positioned from a cross origin behind the joint to attachment points on upper and lower mounting facilities on the upper and lower limbs and provides an opposing tensile force that limits the extension of mounting facilities and the limbs. In embodiments for a knee joint, the brace assembly provides a resisting force to resist hyperextension of the knee. Embodiments of the assembly are able to accommodate different joints, different size wearer's of the assembly and different tension settings such as for athletes during competition. Embodiments of the brace can be used bilaterally and can be made without metal bracing to comply with the requirements of some sports.

24 Claims, 6 Drawing Sheets

(56) References Cited

U.S. PATENT DOCUMENTS

| | | | |
|---|---|---|---|
| 4,702,234 | A | 10/1987 | Huntjens et al. |
| 4,817,588 | A | 4/1989 | Bledsoe |
| 4,854,308 | A * | 8/1989 | Drillio ............................ 602/16 |
| 5,063,916 | A | 11/1991 | France et al. |
| 5,399,153 | A | 3/1995 | Caprio et al. |
| 5,417,647 | A * | 5/1995 | Down ............................ 602/26 |
| 5,512,039 | A | 4/1996 | White |
| 6,368,297 | B1 | 4/2002 | Smits |
| 7,198,610 | B2 | 4/2007 | Ingimundarson et al. |
| 8,007,457 | B2 | 8/2011 | Taylor et al. |
| 8,167,829 | B2 | 5/2012 | Sterling et al. |
| 2002/0010410 | A1 | 1/2002 | Steponovich |
| 2003/0204156 | A1 | 10/2003 | Nelson et al. |
| 2003/0232701 | A1 | 12/2003 | Latella, Jr. |
| 2006/0000478 | A1 | 1/2006 | Taylor |
| 2006/0089583 | A1 * | 4/2006 | Reinhardt ....................... 602/21 |
| 2008/0083055 | A1 | 4/2008 | Onda et al. |
| 2009/0090027 | A1 | 4/2009 | Baudouin et al. |
| 2010/0088803 | A1 | 4/2010 | Orloff et al. |
| 2011/0009793 | A1 | 1/2011 | Lucero et al. |

FOREIGN PATENT DOCUMENTS

| | | |
|---|---|---|
| KR | 100742181 | 7/2007 |
| WO | WO 9400082 A1 * | 1/1994 |
| WO | 2007020372 A2 | 2/2007 |

OTHER PUBLICATIONS

Christopher Geiser, Kristian M. O'Connor, Jennifer E. Earl, Effects of Isolated Hip Abductor Fatigue on Frontal Plane Knee Mechanics, Marquette University e-Publications@Marquette, Health Sciences Faculty Research and Publications, College of Health Sciences, Medicine and Science in Sports and Exercise, vol. 42, No. 3, Mar. 2010, pp. 535-545.

Sue D. Barber-Westin, Stephaine T. Smith, Thomas Campbell, and Frank R. Noyes, The Drop-Jump Video ScreeningTest: Retention of Improvement in Neuromuscular Control in Female Volleyball Players, Journal of Strength and Conditioning Research 2010 National Strength and Conditioning Association, vol. 0, No. 0, Month 2010.

Cale A. Jacobs, Timothy L. Uhl, Carl G. Mattacola, Robet Shapiro, William S. Rayens, Hip Abductor Function and Lower Extremity Landing Kinematics: Sex Differences, Journal of Athletic Training 2007; 42 (1):76-83 by the National Athletic Trainers' Association, Inc. www.journalofathletictraining.org.

Gregory D. Myer, Kevin R. Ford, Joseph P. Palumbo, and Timothy E. Hewett, Neuromuscular Training Improves Performance and Lower-Extremity Biomechanics in Female Athletes, Journal of Strength and Conditioning Research, 2005, 19(1), 51-60, 2005 National Strength & Conditioning Association.

Hawthorne, Ophelia Althea, USPTO Office Action for pending U.S. Appl. No. 13/188,506, 17 pages, mailed Sep. 3, 2013, USA.

Hawthorne, Ophelia Althea, USPTO Office Action for pending U.S. Appl. No. 13/188,506, 17 pages, mailed Aug. 5, 2013, USA.

Hawthorne, Ophelia Althea, USPTO, U.S. Appl. No. 13/188,506, Final Office Action dated Jan. 15, 2014, 11 pages, US.

Hawthorne, Ophelia Althea, USPTO, U.S. Appl. No. 13/188,506, Notice of Allowance dated Apr. 11, 2014, 14 pages, US.

* cited by examiner

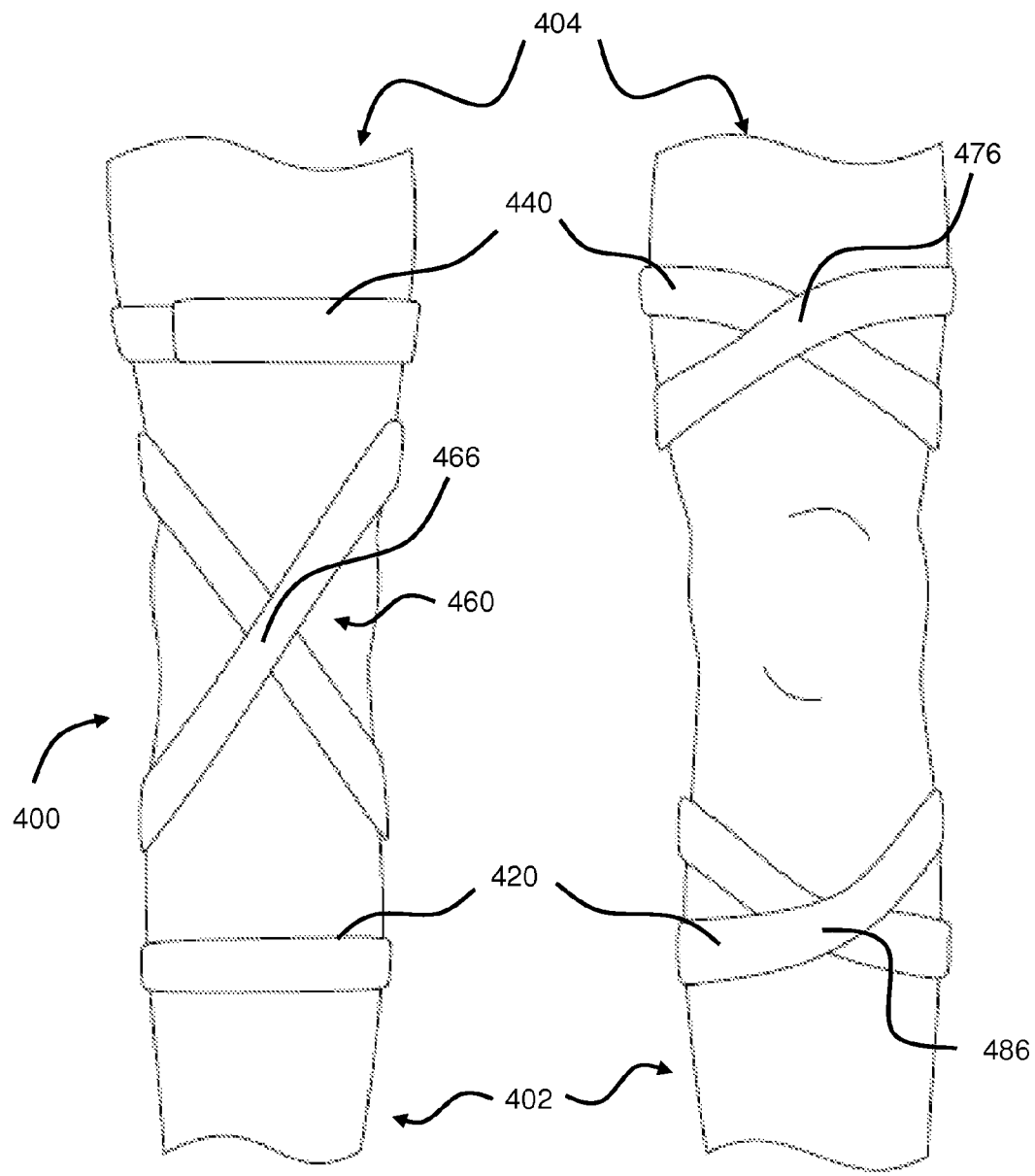
FIG. 4A  FIG. 4B

HYPEREXTENSION BRACE ASSEMBLY AND METHODS OF USE

CROSS-REFERENCE TO RELATED APPLICATIONS

The present application claims the benefit of U.S. Provisional Application Ser. No. 61/058,555, filed Jun. 3, 2008, and entitled "HYPEREXTENSION BRACE ASSEMBLY," and U.S. Provisional Application Ser. No. 61/148,973, filed Feb. 1, 2009, and entitled "HYPEREXTENSION BRACE ASSEMBLY" both of which are herein incorporated herein by reference in their entirety.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

1. Field of the Invention

The present invention relates to braces that can prevent the hyperextension of a joint, and more specifically relates to a knee brace having a cross-strap that assists in preventing hyperextension.

2. Prior Art

Braces are often utilized to support joints when damage, deformation, surgery or the like has caused the joint to be instable. Most of the running, jumping, cutting or twisting sports today have the risk of damaging the knee. These injuries frequently involve a tearing the ACL in the knee. Many injuries to the knee joint have a mechanism of injury of hyperextension in which the ACL is stretched or torn. Many methods have been employed to prevent this action to the knee and prevent the injury to the ACL. Taping techniques as well as rigid braces have been designed to prevent this condition.

One common method of treatment and prevention for these injuries today is the use of the rigid braces. Common to most, if not all, of these devises are, adjustable metal hinges on the medial and lateral side of the knee. Rigid arms on each side connect the hinges to curved thigh and calf pieces or cuffs. A series of Velcro straps attached to these rigid side pieces then wrap around the leg to mount and hold them in place with the cuffs and the hinges. Adjusting the hinge from allowing extension or hyperextension blocks the knee from moving into to these positions quite well.

With respect to these rigid braces however, many sports have rules in which players cannot have any metal or rigid devices on any part of their body to compete due to metal or hard structures that may cause injury to other players. One of these sports is soccer, which is also one of the most popular sports in the world. Additionally, with the introduction of bracing both knees for prevention of injury, the bracing must have a very low profile on the knees to prevent the braces from catching against each other during competition.

Another technique of treating and preventing joint injuries includes taping techniques. While reinforcing joint strength, taping typically does not involve rigid braces that cause problems with sporting rules. Taping techniques have shown some promise for this situation but these techniques still have some of the disadvantages of tape such as loosening, speed of application and rigidity to name just a few disadvantages. Typically, these disadvantages require the wearer to have the tape reapplied to tighten the tape and maintain the desired effect of strengthening the joint.

SUMMARY OF THE INVENTION

Embodiments of the hyperextension brace assembly utilize a cross-strap attached to mounting facilities about a joint to limit the extension of limbs about the joint. The cross-strap assembly is positioned from a cross origin behind the joint to attachment points on upper and lower mounting facilities on the upper and lower limbs and provides an opposing tensile force that limits the extension of mounting facilities and the limbs. In embodiments for a knee joint, the brace assembly provides a resisting force to resist hyperextension of the knee. Embodiments of the assembly are able to accommodate different joints, different size wearer's of the assembly and different tension settings such as for athletes during competition. Embodiments of the brace can be used bilaterally and can be made without metal bracing to comply with the requirements of some sports.

An object of embodiments of the invention is to provide a knee brace assembly having an upper mounting facility for positioning the brace assembly about the thigh area of a user's leg, a lower mounting facility for positioning the brace assembly about the shin area of the user's leg, a hyperextension cross-strap having a cross origin, and the cross-strap is attachable to the upper and lower mounting facilities whereby the cross-strap limits the extension of the upper mounting facility and the lower mounting facility about the joint and cross origin when the cross origin is positioned posterior to the user's knee.

In some embodiments, the cross-strap of the assembly comprises an elastic material having a stretch limit.

In some embodiments, the upper and lower mounting facility are operably connected with a flexible upright comprising a rigid material capable of bending about its longitudinal axis without stretching or compressing along its longitudinal axis.

It is another object of embodiments of the invention to provide a knee brace assembly where the upper mounting facility has an upper mount front portion, the lower mounting facility has a lower mount front portion, the cross-strap further comprising at least two upper arms to connect to the upper mounting facility at an upper attachment point and at least two lower arms to connect to the lower mounting facility at a lower attachment point, the cross-strap having at least two lengths extending along each upper and lower arm and between the upper and lower attachment point, and the cross-strap having an adjusting facility to adjust the at least two lengths.

It is a further object of embodiments of the invention to provide a knee brace assembly where the cross-strap comprises a single strap capable of being woven about the user's leg to create the upper mount front portion, the lower mount front portion, the upper arms, the lower arms and an x-pattern as the cross origin.

It is yet another object of embodiments of the invention to provide a knee brace assembly where the cross-strap comprises at least two straps each strap having an upper and lower end, the two strap upper ends comprise the upper arms and the two strap lower ends comprise the lower arms, and the two straps are capable of being woven about the user's leg to create an x-pattern as the cross origin.

It is an object of embodiment of the invention to provide a knee brace assembly where the cross-strap comprises an x-shaped strap having the cross origin, the at least two upper arms and the at least two lower arms, the lower mounting facility comprises a shin shell having a means to secure the shin shell about the shin area and a means to attach the shin shell to the cross strap arms, or the upper mounting facility comprises a thigh cuff of a knee brace and the lower mounting facility comprises a tibial cuff of a knee brace.

It is another object of embodiments of the invention to provide a knee brace assembly where the upper mounting facility comprises a thigh portion operably connected to a first article of clothing worn by the user and the lower mounting facility comprises a shin shell operably connected to a second article of clothing worn by the user, the upper and lower mounting facilities are connected about a hinge or the upper and lower mounting facilities are connected about a sleeve and a flexible upright.

It is yet another object of embodiments of the invention to provide a knee brace assembly where an orientation of the upper arms between the upper attachment point and the cross origin create an upper tensile force line, an orientation of the lower arms between the lower attachment point and the cross origin comprises a lower tensile force line, and the angle between the upper tensile force line and the lower tensile force line from the cross origin comprises an angle of about 50 to 140 degrees when the brace is worn about the wearer's extended knee.

It is an object of embodiments of the invention to provide a hyperextension brace assembly having an upper mounting facility capable of securing a brace on a user's first limb about a joint, a lower mounting facility capable of securing the brace on a user's second limb about the joint, a cross-strap having at least two arms attachable to the first and second mounting facility, at least one of the arms capable of extending from the lower mounting facility laterally to a position posterior to the joint and continuing medial to the upper attachment point, and at least one of the arms capable of extending from the lower mounting facility medially to a position posterior to the joint and continuing lateral to the upper attachment point whereby the cross-strap is capable of limiting the extension of the user's first and second limb about the joint.

It is another object of embodiments of the invention to provide a hyperextension brace assembly wherein the cross-strap is capable of limiting the extension without the use of a hinge about the joint.

It is an object of embodiments of the invention to provide a method of supporting a wearer's joint, the method comprising the steps of securing an upper mounting facility about the upper limb of the user's joint, securing a lower mounting facility about the lower limb of the user's joint, extending at least one arm of a cross-strap from the lower mounting facility laterally to a position posterior to the joint and continuing medial to the upper mounting facility, and extending at least one arm of the cross-strap from the lower mounting facility medially to a position posterior to the joint and continuing lateral to the upper mounting facility whereby the cross-strap is capable of limiting the extension of the user's first and second limb about the joint.

It is another object of embodiments of the invention to provide a method of supporting a wearer's joint where the step of securing an upper mounting facility comprises securing an upper cuff of a hinged knee brace, and the step of securing a lower mounting facility comprises securing a lower cuff of the hinged knee brace.

BRIEF DESCRIPTION OF THE SEVERAL VIEWS OF THE DRAWINGS

In order that the manner in which the above-recited and other advantages and features of the invention are obtained, a more particular description of the invention briefly described above will be rendered by reference to specific embodiments thereof which are illustrated in the appended drawings. Understanding that these drawing depict only typical embodiments of the invention and are not therefore to be considered to be limiting of its scope, the invention will be described and explained with additional specificity and detail through the use of the accompanying drawings in which:

FIG. 4A illustrates a front view of one embodiment of the brace assembly comprising a single cross-strap about the knee of a wearer.

FIG. 4B illustrates a rear view of one embodiment of the brace assembly comprising a single cross-strap about the knee of a wearer.

DETAILED DESCRIPTION OF THE INVENTION

Although embodiments are described for use with knee bracing and reinforcement, it is understood that the methods and systems described can be used for similar medical situations where support of moving joints may be needed. Notwithstanding the specific example embodiments set forth below, all such variations and modifications that would be envisioned by one of ordinary skill in the art are intended to fall within the scope of this disclosure.

Embodiments of this new brace assembly comprise a non-rigid or semi-rigid brace utilizing a cross-strap to provide a resisting force to joint hyperextension. Embodiments of this brace assembly may optionally include a flexible sleeve or other traditional brace components. Although embodiments of the assembly do not need side hinges or metal upright stays, it is contemplated that embodiments of the brace assembly can also include these elements.

One Embodiment of the Hyperextension Brace Assembly:

Although it is contemplated that embodiments of the assembly can support many different types of skeletal joints such as elbows or knees, the illustrations below will use an embodiment directed to support a person's knee. Therefore, references to anatomical portions of the wearer's knee are for illustration purposes and not as a limitation.

Embodiments of this new brace assembly comprise at least one hyperextension cross-strap, at least one upper mounting facility and at least one lower mounting facility. Generally, the upper mounting facility positions and secures the brace assembly about the thigh area of a user's leg, the lower mounting facility positions and secures the brace assembly about the shin area of the user's leg and the hyperextension cross-strap attaches to the upper and lower mounting facilities whereby the cross-strap can limit the extension of the user's knee when the cross-strap is positioned posterior to the user's knee.

In some embodiments, the brace assembly stabilizes the knee from hyperextension in the 5-25 degree range.

Figures 1A, 1B:
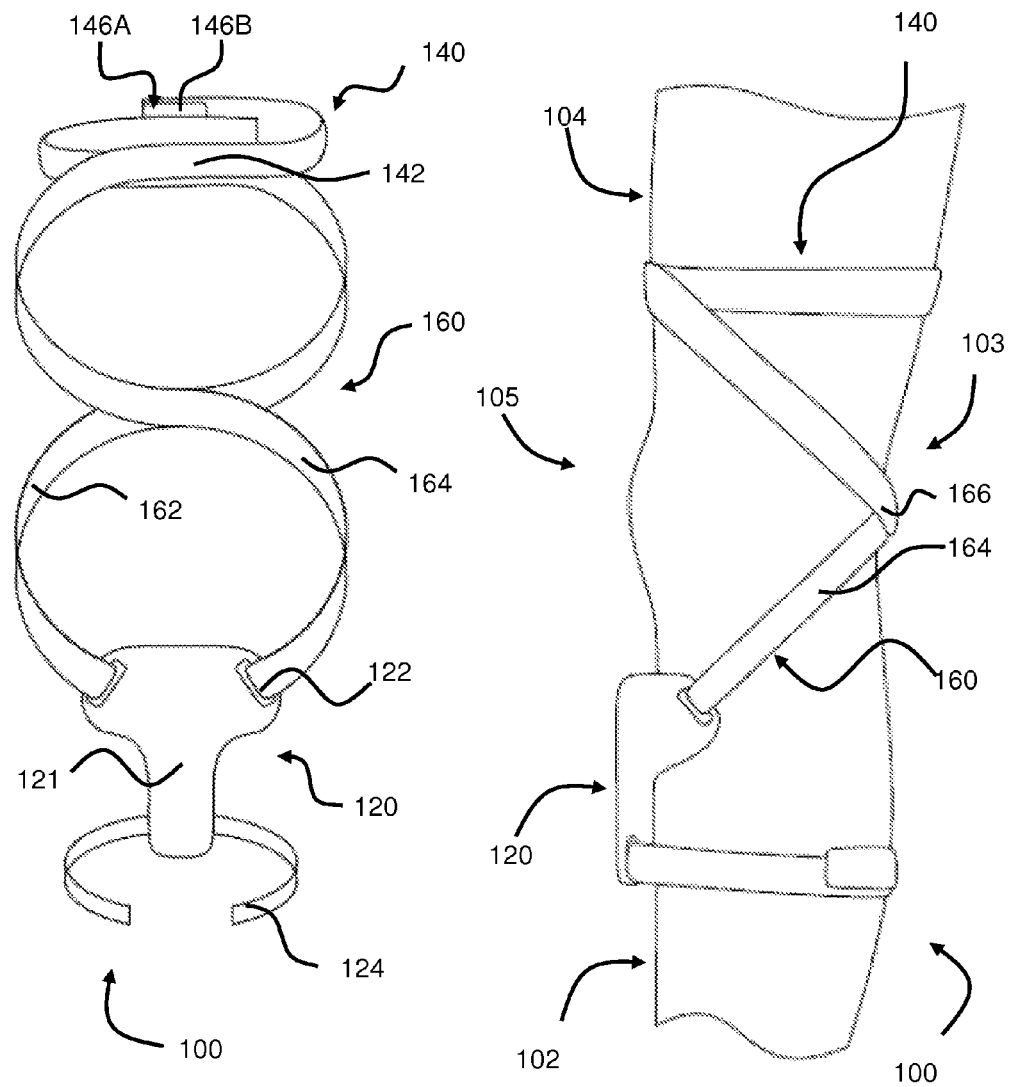
FIG. 1A illustrates a front view of one embodiment of the brace assembly showing a shin shell.
FIG. 1B illustrates a side view of the embodiment the brace assembly of FIG. 1A mounted on the knee of a wearer.

As shown in FIGS. 1A and 1B, the cross-strap 160 is an element able to provide a tensile resistance force and capable of creating a cross pattern that creates a cross origin and strap arms. The cross-strap also comprises means to attach ends of the straps, the strap arms, to the upper and lower mounting facilities. In some embodiments, the cross-strap comprises one or more straps of pre-determined lengths and cross-straps are selected based on the length needed for that wearer. In other embodiments, the cross-strap has adjustment elements that allow the cross-strap to be adjusted to fit the wearer and help prevent joint extension.

The hyperextension cross-strap can be made from material to provide resistance to stretching in one direction. In a preferred embodiment, the cross-strap is a pliable elastic material that provides resistance to a certain limit of stretch and once that limit of stretch, the material provides significantly more resistance, or enough resistance to provide for no more stretch at all. In one embodiment, the cross-strap limit of stretch provides a dampened or soft stop once the limit of stretch is reached. In one embodiment, the elastic material is similar to elastic sports tape. In other embodiments, the elastic material can comprise a rubber material, a plastic material or a spring that acts similar to a rubber band. It is also contemplated that the elastic strap may comprise a combination of elastic and non-elastic material. In embodiments that include a combination of materials, the elastic material can provide elastic resistance while the non-elastic material provides a point of non-elastic resistance. As an example, and not for limitation purposes, these combinations may comprise combinations of cloths, fabrics, threads, struts or other materials combined through sewing, adhesives, Velcro attachment or even simple adjacent placement to elastic materials. Combinations of elastomeric materials with varying resistance properties are also contemplated.

The length, width and elastic properties of the cross-strap can be varied based on the properties desired for the wearer and/or the sport the wearer will participate in. Although some of the discussion relates to a single cross-strap, it is understood that multiple cross-straps or straps can be used to provide the functional properties of the cross-strap. More than on cross-strap or strap can be used such that their properties combine to provide the desired resistance properties.

As shown in FIG. 1A, the cross-strap 160 has two cross-strap arms 162 and 164 respectively configured to connect on a lower arm end to a lower mounting facility 120 at a lower attachment point. The lower mounting facility comprises securing elements, or straps 124 to engage the wearer's lower limb and connect this element to the other elements of the assembly. Embodiments of the lower mounting facility include but are not limited to a hard shell, pad, cuff, portions of the strap, portions of a sleeve or any other element capable of mounting the brace to the wearer's limb. In this embodiment, the lower mounting facility 120 is a shin shell 121 mounted just below the wearer's knee with securing straps 124. In this embodiment, the tibial shell can be made of a flexible material or when desired, it can made of more rigid material to provide some tibial protection to the wearer.

Means to attach the cross-strap arms to the mounting facilities include, but are not limited to rigid fasteners such as rivets, adhesives or sewing; pivoting fasteners such as rivets or buttons; and removable fasteners such as Velcro, buttons, snaps or hooks. It is contemplated that the means of attachment, such as with Velcro straps or buckles, will let the connections be tightened or loosened as desired for comfort or support reasons.

As shown, the connection of the cross-strap is through lower attachment points that comprise multiple openings 122 in the shell positioned so that the cross-strap arms 162 and 164 weave through the shell and extend up towards the wearer's thigh. When installed as in FIG. 1B, these elastic straps extend from the anterior tibia at the patellar attachment and wrap posterior with one wrapping medial and one wrap laterally to attach to the wearer's anterior thigh pad. This "X-strap" configuration creates elastic straps running from lower mounting facility 120, here an anterior tibial pad, with one strap medial and one strut lateral to cross like an X in the popliteal fossa 103 behind the knee 105, then coming back to an anterior of thigh pad 140 in the middle to upper one-third of the thigh.

It is also contemplated that the shin shell can be configured to allow the same straps, or additional straps, clips or bands, to wrap around the wearer's lower leg to secure the lower arms of the cross-strap.

The upper mounting facility positions the brace assembly about the upper limb of a user's joint. Embodiments of this facility can similarly include those possible for the lower mounting facility. In the embodiment shown in FIG. 1, the upper arms of the cross-strap are configured to connect to each other and perform the function of the upper mounting facility 140, much like a thigh pad in a traditional knee brace. In this embodiment, the thigh side connection is made by connectors 146A and 146 B on the end of the upper arms extending up the wearer's thigh. As shown, this connection is made by complementary hook and loop type Velcro fasteners on the thigh end of the straps. In this embodiment, the thigh end of the straps can provide the functionality of a thigh cuff in traditional knee braces by wrapping the straps around the wearer's thigh to help secure the assembly to the thigh. In the embodiment shown, sections of the upper arms also contain optional facility attachment elements 142 that allow the upper arms to connect to the upper mounting facility in particular places. Examples of attachment element can include those possible for the lower mounting facility. In one embodiment, the attachment elements comprise matching Velcro sections attached on the upper arms of the cross-strap. These sections are placed on the cross-strap arms 162 and 164 in pre-determined locations that will allow proper positioning of the elements and help ensure the connection can be maintained anterior to the limb and towards a front portion of the mounting facility.

Figure 2:
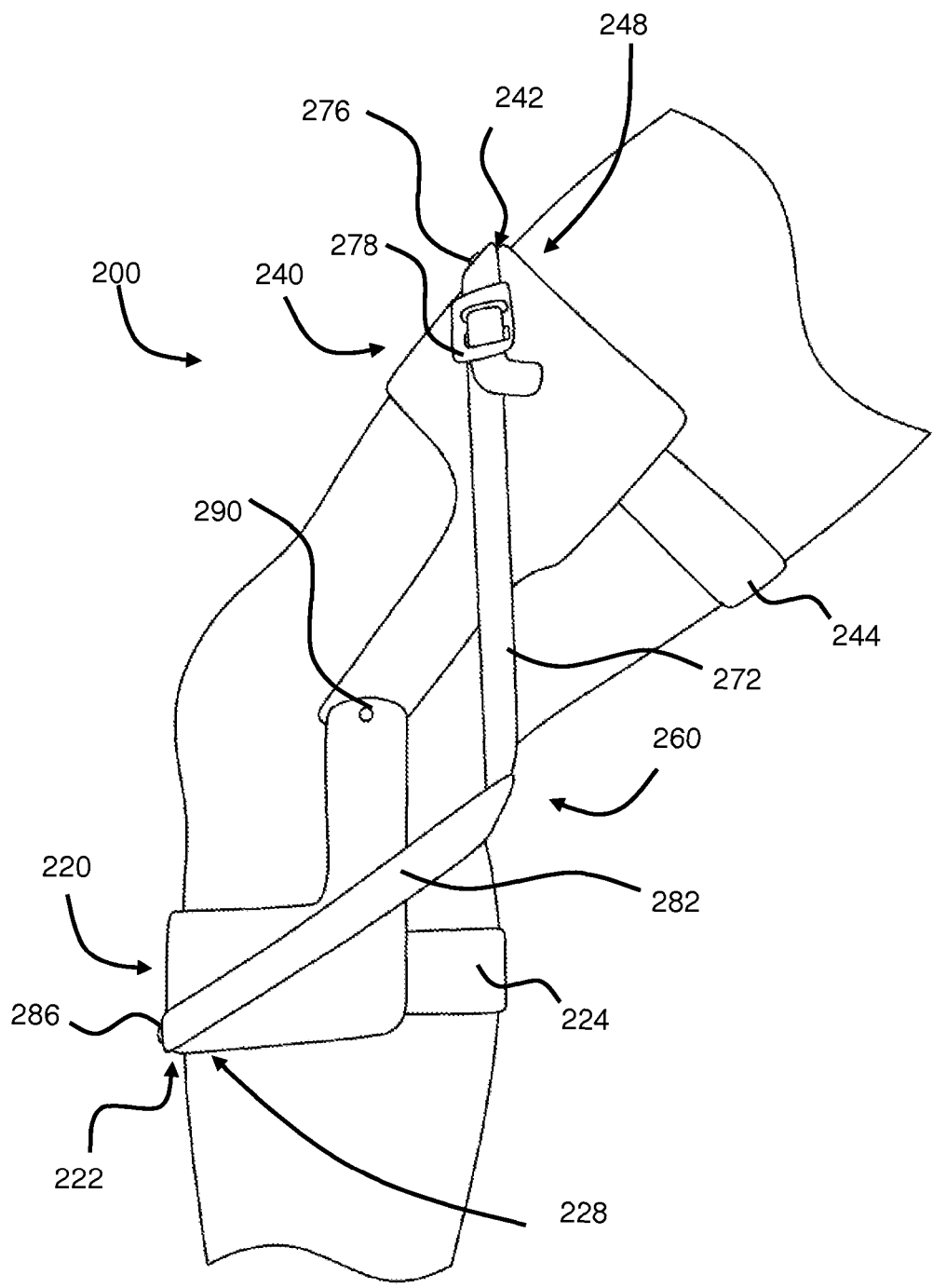
FIG. 2 illustrates a side view of one embodiment of the brace assembly having an upper and lower mounting facility.

In embodiments where the upper mounting facility comprises a thigh pad, as shown in FIG. 2, the thigh pad 240 can comprise any non-rigid material that can engage the wearer's thigh and connect this pad to other elements of the assembly. Suitable materials for this pad include but are not limited to cloth, cotton, plastic, nylon, mesh and leather. This pad may further include padding or may be heat pliable, molded or contoured to be more comfortable for the wearer. The embodiment in FIG. 2 illustrates one embodiment of an anterior thigh pad 240 which can be shaped to the contour of the medial anterior thigh above the vastus medialis oblique.

FIG. 2 also shows that embodiments of the assembly 200 can include a lower mounting facility comprising a tibial pad 220 with similar mechanical characteristics as the thigh pad 240.

In embodiments, as shown in FIG. 2, the mounting facilities 220 and 240 include at least one securing strap 224 and 244 operably connected to the facilities to secure them onto the wearer's limbs. Any means to secure the pads and tighten the pads onto the wearer's body is suitable. In one embodiment, a Velcro type securing strap is attached to each of the pads and when the strap is secured to the pad around the wearer's limb, the pads are secured to the wearer. Other suitable means to secure the facilities to wearer's limbs include but are not limited to a sleeve around the limb and straps with adjusting facilities such as buckles.

It is contemplated that in some embodiments, rather than connecting the cross-strap 260 to the pads, the securing straps 224 and 244 can also provide the connection means for the pads to the elastic straps. For example, the securing strap may have the attachment means and when the securing strap is secured to the pads, the cross-straps are connected to the securing strap.

The cross-strap 260 is attached to the upper and lower mounting facilities at upper and lower facility attachment points 242 and 222. This attachment can be made using any means that will secure the ends of the cross-straps onto the mounting facilities and is generally made at a front portion of the mounting facility. As shown in FIG. 2, the cross-strap arms are permanently connected to the attachment points 242 and 222 on the facility front portions 248 and 228 by rivets at strap attachment points 276 and 286. Connecting means includes any of the connection means already described. If the thigh pad is not used, the cross-straps can be wrapped around the wearer's thigh and connected to themselves to secure the assembly to the wearer.

Figures 3A, 3B:
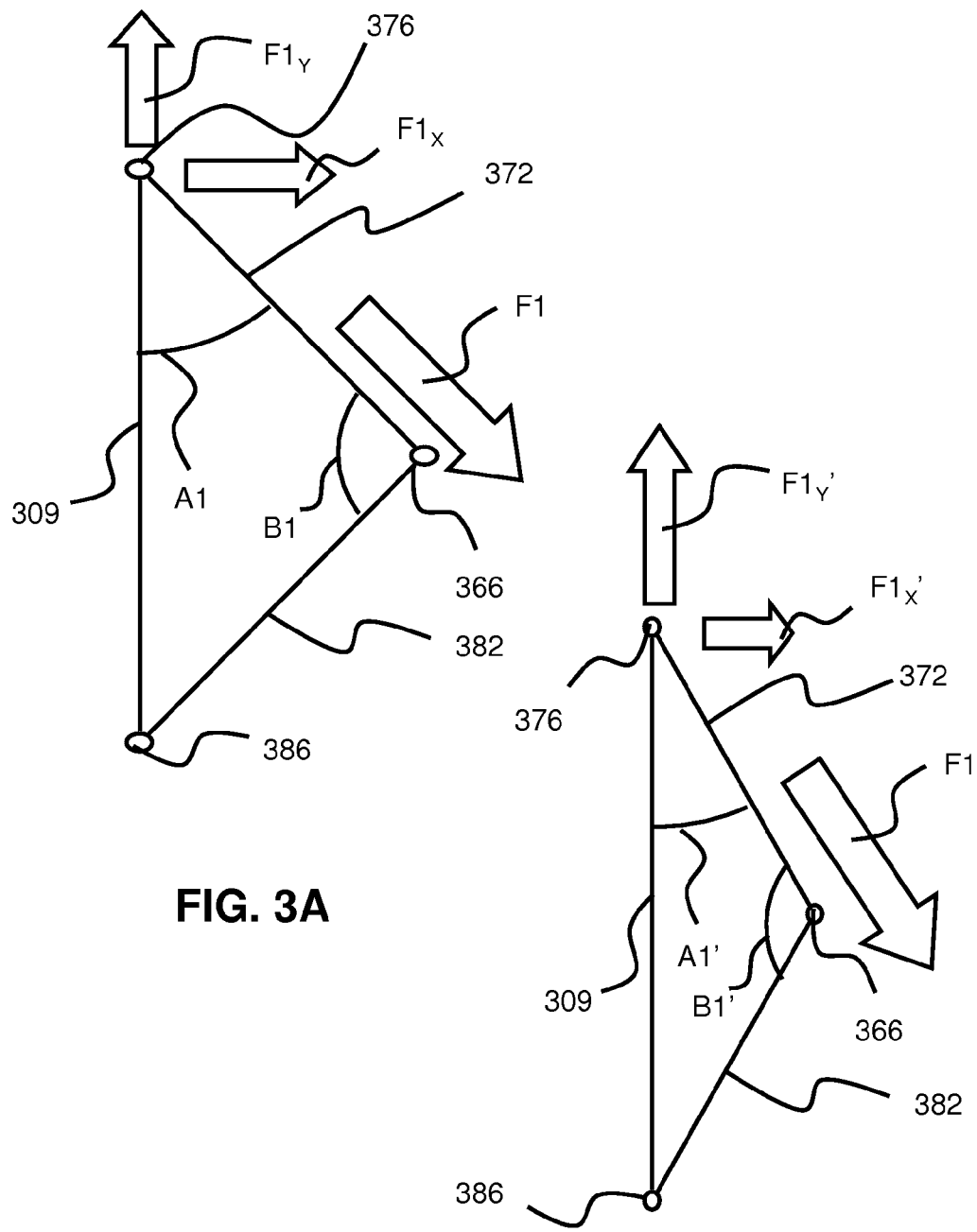
FIG. 3 illustrates the force patterns of one embodiment of the cross-strap when mounted around a knee.

In embodiments of this brace assembly, it is beneficial for the attachment points to be positioned such that the cross-strap can provide a sufficient resistance force at or near the attachment point. When the cross origin is positioned posterior to the joint, this usually means that the attachment points are preferably positioned anterior to the joint at a front portion of the mounting facilities. For example, as represented in FIG. 3A and 3B, this assembly benefits from a configuration that maximizes the tensile force that the cross-straps can provide. In FIG. 3A, the lines 372 and 382 represent the upper and lower cross-strap arms respectively of a cross-strap and the points 376 and 386 represent their strap attachment points and point 366 represents the cross origin. The line 309 generally represents the front part of the wearer's leg. Using the upper strap attachment point 376 as an example, the resistance force F1 that upper cross-strap upper arm 372 provides can be translated into F1subX and F1subY forces as shown. Using trigonometric and static principals, the angle A1 allows the force to be translated in the X direction as F1subX=F1(sinA1). As compared to FIG. 3B, where the angle A1prime of the cross-strap arm 372 to 309 is less than A1, resistance force F1 can be translated into F1subXprime and F1subYprime forces as shown and the resistance force F1subXprime to be applied is less. Therefore, as designed, the attachment of the cross-strap onto the brace assembly towards the anterior, or front portion of the brace, provides more resistance than known prior art brace assemblies with straps.

The resulting angles shown in FIGS. 3A and 3B will vary for each patient given their size, strength in order to control extension of the joint. In some embodiments of the brace assembly, the angle from the lower attachment point and upper attachment point about the cross origin (FIG. 3A angle B1 and FIG. 3B angle B1prime) can be in a range of about 50 to 160 degrees, 60 to 140 degrees or 75 to 115 degrees.

The resulting angles shown in FIGS. 3A and 3B will vary for each patient given their size, strength in order to control extension of the joint. In some embodiments of the brace assembly, the angle from the lower attachment point and upper attachment point about the cross origin (FIG. 3A angle B1) can be in a range of about 50 to 160 degrees, 60 to 140 degrees or 75 to 115 degrees.

Other Embodiments of the Hyperextension Brace:

One embodiment of the brace assembly comprises a single cross-strap mounted in a way that provides the functionality of the brace. As shown in FIGS. 4A and 4B, this embodiment comprises a single cross-strap 460 that is wrapped around the wearer's shin 402 to create the lower mounting facility 420, the arms of the cross-strap are then wrapped behind the knee to cross in the popliteal fossa of the knee to create the cross origin 466. The arms are then extended and wrapped around the wearer's thigh 404 to create the upper mounting facility 440.

In this embodiment of the brace assembly 400, the wrapping around the shin 402 may start with the middle of the cross-strap 460 being placed in the back of the calf. The wrapping can continue around the lower leg once or multiple times. At the point that the cross-strap is extended from a position anterior to the shin and them up behind the knee, there may be elements to help define the strap attachment points 486 to assist in keeping the arms of the cross-strap properly positioned anterior to the joint. The wrapping around the thigh 404 may also be done once or multiple times potentially with elements such as hooks, bands, buttons, loops, Velcro or straps to keep the straps together and define the strap attachment point 476. To close the cross-strap, any connection means already disclosed, such as complementary hook-and-loop connectors can be used to secure the upper arms to each other.

Figure 5:
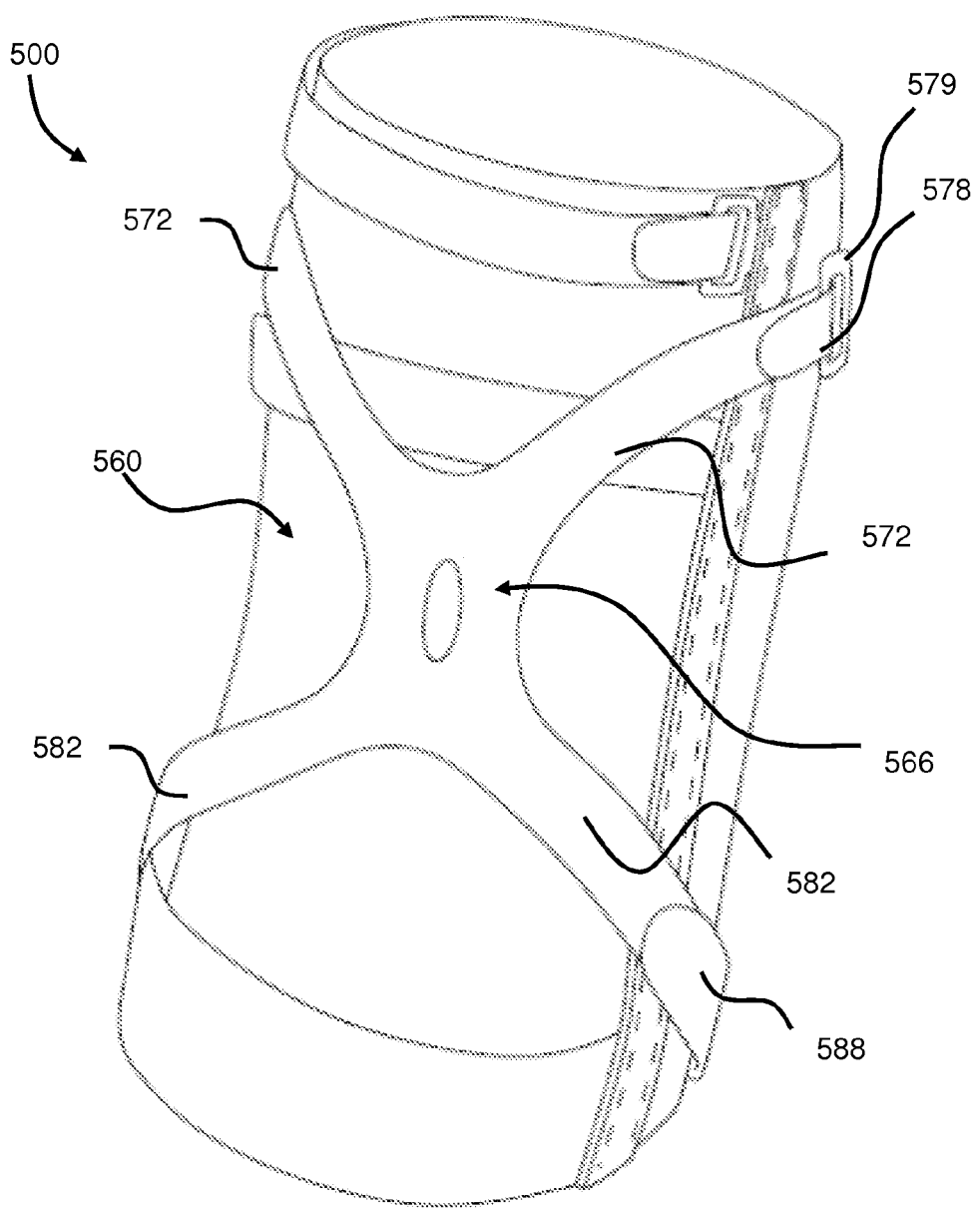
FIG. 5 illustrates a rear view of one embodiment of the brace assembly having an x-shaped cross-strap cooperating with a sleeve.

Another embodiment of the brace assembly utilizes a single x-strap as the cross-strap. As shown in FIG. 5, the assembly 500 has a single x-strap 560 having a cross origin 566, upper arms 572, lower arms 582 and attachment points (shown in FIGS. 6, 673 and 683). This x-strap functions similar to the crossed single cross-strap. As shown, the x-strap arms have Velcro fasteners that act as adjustment elements 578 and 588 on their end. These ends connect through loops 579 that are attached to Velcro fasteners (not shown) on both the upper and lower mounting facility. Adjustment element 578 is able to be pulled through the loops 579 and secured to itself at different positions creating arms of different lengths. In one embodiment, this x-strap is long enough to extend from the anterior tibia at the patellar attachment and wrap posteriorly with one arm wrapping medial and one wrapping laterally to attach to the wearer's anterior thigh pad. This "X-strap" configuration creates arms running from an anterior tibial pad with one strap medial and one strap lateral to cross like an X in the popliteal fossa of the knee, then coming back to an anterior thigh pad in the middle to upper one-third of the thigh.

Similarly, embodiments having two straps can be made where two elastic straps are used to create the cross-strap.

Figure 6:
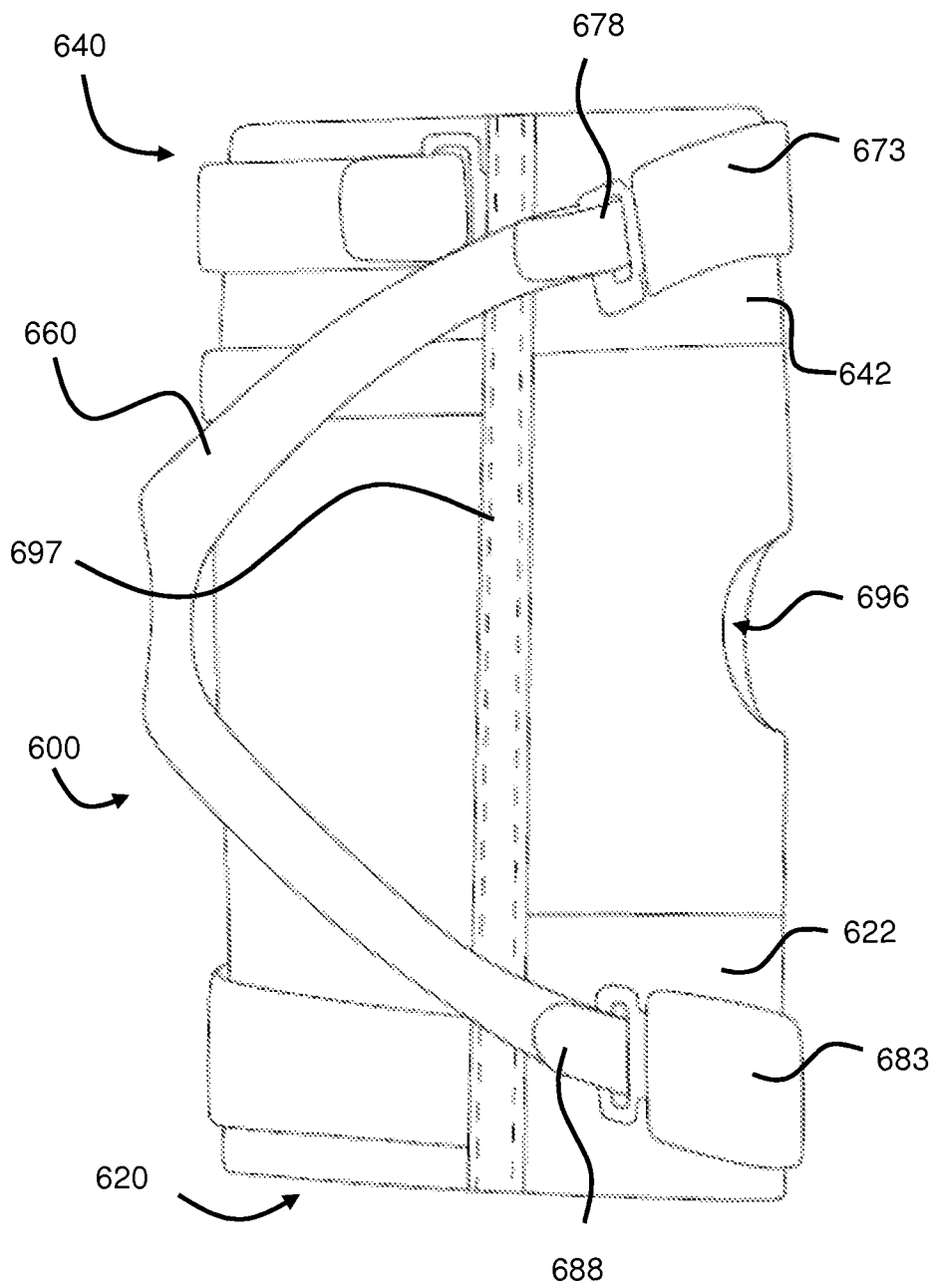
FIG. 6 illustrates a side view of one embodiment of the brace assembly showing the cross-strap attachment to the upper and lower mounting facilities on a sleeve.

Embodiments of a brace assembly also include having a brace sleeve to provide assembly elements. This type of embodiment is shown in FIGS. 5 and 6. In FIG. 6, the upper and lower portions of the sleeve, 640 and 620 can function as the including the upper and lower mounting facilities respectively. The sleeve in these embodiments will rest against the wearer's skin. The surface of the sleeve that will touch the wearer's skin, the under sleeve, is a non-slick surface to frictionally engage the wearers limb. In the embodiment of FIG. 6, the inner surface of the sleeve 696 comprises an open faced diamond shaped web weave that frictionally engages the skin and also allows portions of the skin surface to be exposed. Other embodiments of the frictional surface of the under sleeve include but are not limited to high friction surfaces such as rubber, felt, mesh or any combination of these surfaces. It is contemplated that under sleeve material can be used so that the under sleeve is in contact with the skin around the knee under the elastic straps to help keep them in place.

As shown in FIG. 6, embodiments of the brace assembly 600 can include additional fasteners 673 and 683. These fasteners provide the connection between the upper and lower mounting facilities and the ends of the cross-strap 660 and function as the strap attachment points. With this configuration, the facility attachment points 642 and 622 on the mounting facilities comprises an entire anterior area of the brace having hook-and-loop type fasteners that can match with the under surface of the fasteners 673 and 683. In this configuration, the placement of the fasteners 673 and 683 up and down length of the brace adjusts the effective length of the cross-strap about the wearer's knee. This adjustment can be used in cooperation with the adjustment from the adjustment elements 678 and 688 to adjust the length of the cross-strap. Although these additional fasteners can be a separate element from the cross-strap and the strap arms, they function as an extension of the cross-strap.

Embodiments of the brace assembly without metallic or rigid elements able to comply with current sporting regulations, such as the FIFA rules.

The embodiment shown in FIG. 6 also includes optional flexible uprights 697 on one or both sides of the brace. An upright as used in this description is a hinge that has a high degree of axial stiffness and a high degree of bending flexibility. Examples of suitable uprights would be coiled spring cables, chain links or ball-and-socket links, planar struts or flexible struts that prevent the upper and lower mounting facilities from urging towards each other when the assembly is subjected to the forces of the elastic straps. The upright has the capability to bend in one or more planes while not compressing. The upright can be directly connected to the pads, sewn into the sleeve or be attached to other elements that are connected to the pads to keep the pads from urging towards each other. In these embodiments, suitable material for the uprights include, but is not limited to metals, Kevlar or carbon fiber type construction that will provide flexibility but not let the upright compress. Suitable overall shapes for the upright include but are not limited to a flexible rod that easily allows flexing of the knee when the uprights are installed on the wearer's leg.

Embodiments of the brace assembly can also include traditional knee braces elements such as upper and lower frames with central hinges as well as structures for patellar control. The cross-strap could be added to these assemblies to provide additional support and hyperextension protection. As shown in FIG. 2, the cross-strap 260 can function with a thigh cuff 240 and a tibia cuff 220. The cross-strap crosses behind the knee and the arms attach to the facility attachment points 242 and 222 on the cuffs. The hinge 290 of the brace can be of any type uses with traditional braces to include, but not limited to monocentric of polycentric hinges.

One embodiment of the brace assembly further comprises configuring the tibial pad to function as an endo-skeleton such as with a wearer's shin guard, as may be required in a sport such as soccer, to support anterior tibia and anterior drawer control.

Although not necessary, it is contemplated that some embodiments of the assembly can be capable of being integrated with a patellar control-open patellar donut as prescribed. In these embodiments, the assembly may include straps for patellar subluxation that stabilizes the cross-strap or hinges.

Although not necessary, in some embodiments of the assembly, the assembly further includes a covering that can be decorative and/or can provide a sleek/smooth surface for the wearer.

Although the above description and terminology of the components of the embodiments above utilize the terminology of a knee, it is understood and contemplated that the assembly can be applied to other joints. For example, one embodiment of the assembly can be used with a persons elbow joint.

One Embodiment of the Hyperextension Brace Assembly in Operation:

One embodiment of the disclosed inventions will be used to further illustrate the operational aspects of the invention. Although the embodiment discussed utilizes an assembly embodiment with a shin shell as the lower mounting facility, it is understood that embodiments of the invention can be applied to an assembly without a shin shell. For those other embodiments, such as shown in FIG. 5, the connection of the straps on or around the wearer's thigh in a sleeve provides many of the same functions as the upper mounting facility described below.

One embodiment of the invention, as shown in FIGS. 1A and 1B, is used about a wearer's knee 105. The brace assembly 100 is initially secured on the wearer's shin 102. This is done by securing the shin shell 120 on the shin 102 and wrapping the securing straps 124 around the calf. This securing is done at a point of that calf such that the movement of the shell towards the knee is minimized. Once secured on the shin, the cross-strap arms 162 and 164 are wrapped behind the knee creating an x-pattern as the cross origin 166 in the popliteal fossa of the knee and then wrapped anterior and around the thigh. Velcro connectors 146A and 146B of the strap arms 162 and 164 are secured to each other forming the upper mounting facility 140. The upper arms of the cross-strap are attached to matching Velcro fasteners on the cross-strap such that they create facility attachment point 142 anterior on the thigh. As with the shin shell 120, the placement of the upper mounting facility 140 is done to minimize the movement of the facility towards the knee 105.

Once secured on the thigh 104 and the tibia, the presence of the elastic straps in the X configuration helps prevent the knee from hyperextension. Hyperextension is prevented by the cooperation of the secured ends of the straps with positioning of the straps behind the knee. The elastic straps stretch up to a point of knee extension and when reaching a desired limit, the elastic straps reach their limit of extension. The point of connection, facility attachment points 142 and 122, of the elastic straps and the thigh and tibial pad respectively are such that the desired resistance allows proper knee movement but prevents hyperextension. Additionally, if the brace assembly 100 has good frictional contact with the skin, rotational support of the knee joint is also provided. As the wearer uses the brace assembly, and as their need for support and/or comfort changes, the elastic straps can be tightened or loosened simply to removing and reattaching the straps with the Velcro attaching means.

The embodiment of FIG. 4 operates similarly. In this embodiment, the cross-strap 460 is used to function as both the lower mounting facility 420 and the upper mounting facility 440. This can start with the cross-strap being initially wrapped around the shin 402 of the wearer and crossing the arms around each other anterior to the shin. Once secured on the shin 402, the same methods described for FIG. 1 can be followed to mount the brace assembly on the knee.

Other Embodiments of the Hyperextension Brace Assembly in Operation:

The embodiments of FIGS. 2, 5 and 6 operate in a similar manner to those shown in FIGS. 1 and 4. With the embodiments of FIGS. 2, 5 and 6, the upper and lower cuff or the sleeve is mounted around the knee and the cross-strap is attached to the attachment points and adjusted. The cross-straps can be adjusted so that the length of the upper and lower arms between the attachment points is made longer or shorter depending on the person wearing the brace assembly. In embodiments, the uprights can be contained within the under sleeve or other covering that connects the hinges to the upper and lower pad. The placement of the uprights maintain the relative distance between the upper and lower pad and therefore helps maintain the resistance and support provided by the elastic straps.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. Although this invention has been described in the above forms with a certain degree of particularity, it is understood that the present disclosure has been made only by way of example and numerous changes in the details of construction and combination and arrangement of parts may be resorted to without departing from the spirit and scope of the invention.

We claim:

1. A knee brace assembly comprising:
a hyperextension cross-strap having a cross origin;
the cross-strap defining a first wrap of the cross-strap adapted to wrap around a user's leg as an upper mounting facility for positioning the brace assembly about a thigh area of a user's leg;
a lower mounting facility for positioning the brace assembly about a shin area of the user's leg;
the cross-strap comprises an elastic material; and
the cross-strap extending from the upper mounting facility to the lower mounting facility to define a second wrap of the cross-strap adapted to wrap around the user's leg whereby the cross-strap limits an extension of the upper mounting facility and the lower mounting facility about the cross origin without a hinge when the cross origin is positioned posterior to the user's knee.

2. The knee brace assembly of claim 1 wherein:
the upper mounting facility having an upper mount front portion;
the lower mounting facility having a lower mount front portion;
the cross-strap further comprising at least two upper arms extending from the upper mounting facility at an upper attachment point on the upper mount front portion and at least two lower arms to attach to the lower mounting facility at a lower attachment point on the lower mount front portion.

3. The knee brace assembly of claim 2 wherein:
the cross-strap comprises a single strap capable of being woven about the user's leg to create the upper mount front portion, the lower mount front portion, the upper arms, the lower arms and an x-pattern as the cross origin.

4. The knee brace assembly of claim 2 wherein:
the cross-strap comprises an x-shaped strap having the cross origin, the at least two upper arms and the at least two lower arms.

5. The knee brace assembly of claim 2 wherein:
the lower mounting facility comprises a shin shell having a means to secure the shin shell about the shin area and a means to attach the shin shell to the cross strap arms.

6. The knee brace assembly of claim 2 wherein:
the upper mounting facility further comprises a thigh cuff of a knee brace; and
the lower mounting facility comprises a tibial cuff of a knee brace.

7. The knee brace assembly of claim 2 wherein:
the upper mounting facility further comprises a thigh portion operably connected to a first article of clothing worn by the user; and
the lower mounting facility comprises a shin shell operably connected to a second article of clothing worn by the user.

8. The knee brace assembly of claim 2 wherein:
an orientation of the upper arms between the upper attachment point and the cross origin create an upper tensile force line;
an orientation of the lower arms between the lower attachment point and the cross origin comprises a lower tensile force line; and
the angle between the upper tensile force line and the lower tensile force line from the cross origin comprises an angle of about 50 to 140 degrees when the brace is worn about the wearer's extended knee.

9. A hyperextension brace assembly comprising:
a cross-strap defining a first wrap of the cross-strap adapted to wrap around a user's first limb about a joint as an upper mounting facility capable of securing a brace on the user's first limb;
a lower mounting facility capable of securing the brace on a user's second limb about the joint;
the cross-strap having two or more arms extending from the upper mounting facility to lower mounting facility;
the cross-strap comprises an elastic material;
at least one of the arms capable of extending from the lower mounting facility laterally to a position posterior to the joint and continuing medial to the upper mounting facility;
at least one of the arms capable of extending from the lower mounting facility medially to a position posterior to the joint and continuing lateral to the upper mounting facility; and
the two or more arms capable of extending in the position posterior to the joint to create an x-pattern as a cross origin in a fossa of the joint to define a second wrap of the cross-strap adapted to wrap around the user's joint whereby the cross-strap is capable of limiting an extension of the user's first and second limb about the joint without a hinge.

10. The hyperextension brace assembly of claim 9 wherein:
the two or more arms of the cross-strap having an upper end and a lower end;
the user's first limb comprises a thigh about a knee;
the upper mounting facility comprises the arm upper ends capable of wrapping around the user's thigh and connecting to each other;
the user's second limb comprises a shin; and
the lower mounting facility comprises a shin shell having a shin securing strap.

11. The hyperextension brace assembly of claim 9 wherein:
the at least two arms of the cross-strap having an upper end and a lower end;

the user's first limb comprises a thigh about a knee;
the upper mounting facility further comprises a securing device on an article of clothing of the wearer;
the user's second limb comprises a shin; and
the lower mounting facility comprises a securing device on an article worn by the wearer.

12. The hyperextension brace of claim 9 wherein:
the upper mounting facility having an upper mount front portion;
the lower mounting facility having a lower mount front portion;
the upper arms extending from the upper mounting facility at an upper attachment point on the upper mount front portion and the lower arms attach to the lower mounting facility at a lower attachment point on the lower mount front portion; and
the cross-strap limits the extension of the user's first and second limb about the joint by limiting the extension of the upper mount front portion and the lower mount front portion relative to a cross origin.

13. The knee brace assembly of claim 1 wherein:
the cross-strap further comprising at least two upper arms extending from the upper mounting facility and at least two lower arms to attach to the lower mounting facility;
the cross-strap comprises at least two straps each strap having an upper and lower end;
the two strap upper ends comprise the upper arms and the two strap lower ends comprise the lower arms; and
the two straps are capable of being woven about the user's leg to create an x-pattern as a cross origin.

14. The knee brace assembly of claim 1 wherein:
the cross-strap further comprising at least two upper arms extending from the upper mounting facility and at least two lower arms to attach to the lower mounting facility;
the cross-strap having at least two lengths extending along each upper and lower arm and between the upper attachment point and the lower attachment points; and
the cross-strap having an adjusting facility to adjust the at least two lengths.

15. A method of supporting a user's joint, the method comprising:
securing a lower mounting facility about a lower limb of the user's joint;
extending a first arm of a cross-strap from the lower mounting facility laterally to a position posterior to the joint and continuing medial to an upper attachment point;
extending a second arm of the cross-strap from the lower mounting facility medially to a position posterior to the joint and continuing lateral to the upper attachment point; and
extending one or both of the first and second arm of the cross-strap posterior to an upper limb of the user's joint and coupling the first and second arm of the cross-strap to define an upper mounting facility secured about the upper limb of the user's joint whereby the cross-strap is capable of limiting an extension of the upper limb and the lower limb about the user's joint.

16. The method of claim 15 wherein:
securing the upper mounting facility further comprises securing an upper cuff of a hinged knee brace; and
securing the lower mounting facility further comprises securing a lower cuff of the hinged knee brace.

17. The method of claim 15 wherein;
the step of securing a lower mounting facility comprises securing a shin shell about the lower limb of the user's joint.

18. A knee brace assembly comprising:
an upper mounting facility for positioning the brace assembly about a thigh area of a user's leg;
a lower mounting facility for positioning the brace assembly about a shin area of the user's leg;
a hyperextension cross-strap having a cross origin;
the cross-strap further comprising two or more arms configured to attach to each other and define one of the upper or lower mounting facilities; and
the cross-strap being attachable to the upper and lower mounting facilities whereby the cross-strap limits an extension of the upper mounting facility and the lower mounting facility about the cross origin when the cross origin is positioned posterior to the user's knee.

19. The knee brace assembly of claim 18 wherein the upper and lower mounting facilities are connected about a hinge.

20. The knee brace assembly of claim 18 wherein the upper mounting facility and the lower mounting facility are operably connected by a flexible upright.

21. The knee brace assembly of claim 18 wherein the upper and lower mounting facilities comprise an upper and lower portion of a sleeve having a flexible upright.

22. The knee brace assembly of claim 18 wherein the cross-strap comprises a single strap capable of being woven about the user's leg to create the upper mount front portion, the lower mount front portion, the upper arms, the lower arms and an x-pattern as the cross origin.

23. A knee brace assembly comprising:
a hyperextension cross-strap having a cross origin;
the cross-strap defining an upper mounting facility for positioning the brace assembly about a thigh area of a user's leg;
the upper mounting facility having an upper mount front portion;
a lower mounting facility for positioning the brace assembly about a shin area of the user's leg;
the lower mounting facility having a lower mount front portion;
the cross-strap being extending from the upper mounting facility to the lower mounting facility whereby the cross-strap limits an extension of the upper mounting facility and the lower mounting facility about the cross origin without a hinge when the cross origin is positioned posterior to the user's knee; and
the cross-strap further comprising at least two upper arms extending from the upper mounting facility at an upper attachment point on the upper mount front portion and at least two lower arms to attach to the lower mounting facility at two lower attachment points on the lower mount front portion.

24. The knee brace assembly of claim 23 wherein:
the cross-strap comprises at least two straps each strap having an upper and lower end;
the two strap upper ends comprise the upper arms and the two strap lower ends comprise the lower arms; and
the two straps are capable of being woven about the user's leg to create an x-pattern as a cross origin.

* * * * *

UNITED STATES PATENT AND TRADEMARK OFFICE
CERTIFICATE OF CORRECTION

PATENT NO. : 8,852,133 B2  Page 1 of 1
APPLICATION NO. : 12/993258
DATED : October 7, 2014
INVENTOR(S) : Lonnie E. Paulos et al.

It is certified that error appears in the above-identified patent and that said Letters Patent is hereby corrected as shown below:

Title Page, Item (73) Assignee, "Pavlos" should read "Paulos".

Signed and Sealed this
Seventeenth Day of March, 2015

Michelle K. Lee
*Director of the United States Patent and Trademark Office*